US006218144B1

(12) United States Patent
Scott et al.

(10) Patent No.: US 6,218,144 B1
(45) Date of Patent: Apr. 17, 2001

(54) COSTAL2 GENES AND THEIR USES

(75) Inventors: Matthew P. Scott, Stanford; John C. Sisson, Santa Cruz, both of CA (US)

(73) Assignee: The Board of Trustees of The Leland Stanford Junior University, Palo Alto, CA (US)

(*) Notice: Subject to any disclaimer, the term of this patent is extended or adjusted under 35 U.S.C. 154(b) by 0 days.

(21) Appl. No.: 09/098,901

(22) Filed: Jun. 17, 1998

Related U.S. Application Data

(60) Provisional application No. 60/051,347, filed on Jun. 30, 1997.

(51) Int. Cl.$^7$ .......................... C07H 21/02; C07H 21/04; C12N 15/00; C12N 15/63; C12P 21/06

(52) U.S. Cl. .................. 435/69.1; 435/320.1; 435/325; 435/455; 536/23.1; 536/23.5

(58) Field of Search .......................... 536/23.1; 435/325, 435/320.1, 170.1, 170.2

(56) References Cited

U.S. PATENT DOCUMENTS 5,770,443 * 6/1998 Kiefer et al. .......................... 435/325

OTHER PUBLICATIONS

Li et al. GenBank Accessiion No. U45285, Mar. 25,1996.*
Simpson et al., Developmental Biology, vol. 122, p. 201–209, 1987.*
Alexandre, Cyrille, et al., "Transcriptional Activation of Hedgehog Target Genes In Drosophila Is Mediated Directly By The Cubitus Interrupts Protein, A Member Of The GLI Family Of Zinc Finger DNA–Binding Proteins," *Genes & Development* (1996) vol. 10:2003–2013.
Chen, Yu, et al., "Dual Roles For Patched In Sequencing And Transducing Hedgehog," *Cell* (Nov. 1, 1996) vol. 87:553–563.
Chiang, Chin, et al., "Cyclopia And Defective Axial Patterning in Mice Lacking Sonic Hedgehog Gene Function," *Nature* (Oct. 3, 1996) vol. 383:407–413.
Dominguez, Maria, et al., "Sending And Receiving The Hedgehog Signal: Control By The Drosophila Gli Protein Cubitus Interrupts," *Science* (Jun. 14, 1996) vol. 272:1621–1625.
Ericson, Johan, et al., "Two Critical Periods Of Sonic Hedgehog Signaling Required For The Specification Of Motor Neuron Identity," *Cell* (Nov. 15, 1996) vol. 87, No. (4):661–673.
Gailani, Mae R., et al., "The Role Of The Human Homologue of Drosophila Patched In Sporadic Basal Cell Carcinomas," *Nature Genetics* (Sep. 1996) vol. 14:78–81.
Goldstein, Lawrence S.B., "With Apologies To Scheherazade: Tails Of 1001 Kinesin Motors," *Annu. Rev. Genet.* (1993) vol. 27:319–51.

Hahn, Heidi, et al., "Mutations Of The Human Homolog Of Drosophila Patched In The Nevoid Basal Cell Carcinoma Syndrome," *Cell* (Jun. 14, 1996) vol. 85:841–851.
Heitzler, Pascal, et al., "Genetic And Cytogenetic Analysis Of The 43A–E Region Containing The Segment Polarity Gene *Costa* And The Cellular Polarity Genes Prickle And Spiny–Legs In *Drosophila Melanogaster*, " *Genetics* (Sep. 1993) vol. 135:105–115.
Hepker, Jennifer, et al., "*Drosophila Cubitus Interruptus* Forms A Negative Feedback loop With Patched And Regulates Expression Of Hedgehog Target Genes," *Development* (1997) vol. 124:549–558.
Johnson, Ronald L., et al., "Human Homolog Of Patched, A Candidate Gene For The Basal Cell Nevus Syndrome," *Science* (Jun. 14, 1996) vol. 272:1668–1671.
Kull, F. Jon, et al., "Crystal Structure Of The Kinesin Motor Domain Reveals A Structural Similarity To Myosin," *Nature* (Apr. 11, 1996) vol. 380:550–555.
Marigo, Valeria, et al., "Biochemical Evidence that Patched Is The Hedgehog Receptor," *Nature* (Nov. 14, 1996) vol. 384:176–179.
Marigo, Valeria, et al., "Cloning, Expression, And Chromosomal Location Of SHH And IHH: Two Human Homologues Of The Drosophila Segment Polarity Gene Hedgehog," *Genomics* (1995) vol. 28:44–51.
Préat, Thomas, et al., "Segmental Polarity In *Drosophila Melanogaster*: Genetic Dissection Of Fused In A Suppressor Of Fused Background Reveals Interaction With Costal–2," *Genetics* (Dec. 1993) vol. 135:1047–1062.
Stone, Donna M., et al., "The Tumour–Suppressor Gene Patched Encodes A Candidate Receptor For Sonic Hedgehog," *Nature* (Nov. 14, 1996) vol. 384:129–134.
Tucker, Carla, et al., "Probing The Kinesin–Microtubule Interaction*," *The Journal of Biological Chemistry* (Apr. 4, 1997) vol. 272, No. (14):9481–9488.
Von Ohlen, Tonia, et al., "Hedgehog Signaling Regulates Transcription Through Cubitus Interrupts, A Sequence–Specific DNA Binding Protein," *Proc. Natl. Acad. Sci. USA* (Mar. 1997) vol. 94:2404–2409.
Whittle, J. R.S., "Costal: A Mutant Producing Duplications In The Wing Of Drosophila," *Heredity* (Aug. 1974) vol. 33, No.(1):139.

* cited by examiner

*Primary Examiner*—Karen M. Hauda
*Assistant Examiner*—Shin-Lin Chen
(74) *Attorney, Agent, or Firm*—Pamela J. Sherwood; Paula A. Borden; Bozicevic, Field & Francis, LLP

(57) ABSTRACT

Methods for isolating costal2 genes are provided. The costal2 nucleic acid compositions find use in identifying homologous or related proteins and the DNA sequences encoding such proteins; in producing compositions that modulate the expression or function of the protein; and in studying associated physiological pathways. In addition, modulation of the gene activity in vivo is used for prophylactic and therapeutic purposes, such as identification of cell type based on expression, and the like.

7 Claims, 2 Drawing Sheets

```
1     MEIPIQVAVRIFPHRELKDLLRSFGPTEPKKDAQAVDEGADSKDSEAQVP
51    AAEKDNPSISETDPNGNAEQDSAADSKTIPDANGNDSGQKDYPDSAYCVQ
101   AIPISASALGLPSALPGGDPMDSIAAGLIQVGPHTVPVTHALPSSSSQEQ
151   VYHQTVFPLITLFLEGFDASVVT[YGQRGQGK]SYTLYGNVQDPTLTDSTEG
201   VVQLCVRDIFSHISLHPERTYAINVGFVEICGGDVC[DLL]GMGNIHCTNVD
251   AVFHWLQVGLSARQ SLPAH TLFTLTLEQQWVSKEGLLQHRLSTASFS DLC
301   GTER CGDQPPGRPLDAGLCMLEQVISTLTDPGLMYGVNG[NIPYGQ]TTLTT
351   LLKDSFGGRAQTLVILCVSPLEEHLPETLGNLQFAFKVQCVRNFVIMNTY
401   SDDNTMIVQPAEPVPESNSSAGPLSQAGPGDNFGLQFAASQWSKLVTNAE
451   GLFSKLIDSKLITEVEKEQIDEWLFLKQECEECLSSTEAMRQQKQLVPIL
501   EAEEPEDVNSEAANSESPNSDNENDTDNESHRPDLDDKIESLMEEFRDKT
551   DALILEKHAEYLSKHPKAVMQSQDREIEAQPPEENGDDRKVSIGSRRRSV
601   QPGASLSTAELAMLNRVASQQPPPPIDPESVVDPLESSSGEG IRQAALAA
651   AAATAPIEQLQKKLRKLVAEIEGKQRQLREIEETIQVKQNIIAELVKNSD
701   TRSHAKQRFHKKRAKLEAECDKAKKQLGKALVQGRGQSEIERWTTIIGHL
751   ERRLEDLSSMKHIAGESGQKVKKLQQSVGESRKQADDLQKKLRKECKLRC
801   QMEAELVKLRESRETGKELVKAQGSPEQQGRQLKAVQARITHLNHILREK
851   SDNLEXQPGPEQQETLRHEIRNLRGTRDLLLKERCHLDRKLKRDKVLTQK
901   EERKLLECDEAIEAIDAAIEFKNEMITGHRSIDTSDRIQREKGEQMLMAR
951   LNRLSTEEMRTLLYKYFTKVIDLRDSSRKLELQLVQLERERDAWEWKERV
1001  LSNAVRQARLEGERNAVLLQRQHEMKLTLMLRHMAEETSASSASYGERAL
1051  APACVAPPVQASSDFDYDHFYKGGGNPSKALIKAPKPMPTGSALDKYKDK
1101  EQRSGRNIFAKFHVLTRYASAAAAGSSGSTAEESTALIESTTTATATTTS
1151  TTTTGAVGKVKDKALVSFRPEQLKRLMPAPTATKVTRQKNKIIIQDASRR
1201  N
```

Globular Head — Coiled-coil — Globular Tail

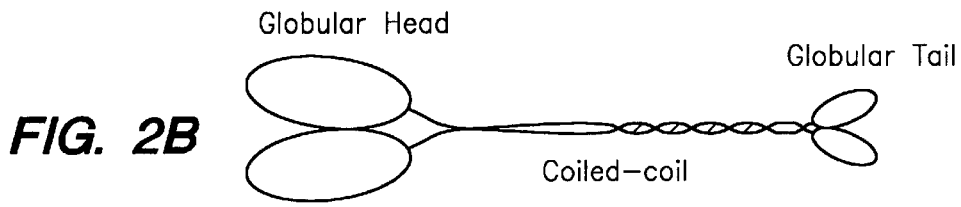

FIG. 2C

| | P-loop Alignment | Motor Domain identity (%) |
|---|---|---|
| Cos2 | LEGFDASVVTYGQRGQGKSYTLYG | 100 |
| BimC | LAGYNCTIFAYGQTGTGKTYTMSG | 28 |
| HuKhc | LEGYNGTIFAYGQTSSGKTHTMEG | 28 |
| Kif3 | LEGYNGTIFAYGQTGTGKTFTMEG | 28 |
| KipA | LDGYNVCIFCYGQTGSGKTHTMYS | 30 |
| Smy1 | LNGYNGTVITYGPSFSGKSYSLIG | 27 |
| Unc-104 | FEGYNVCIFAYGQTGSGKSYTMMG | 28 |
| DmKhc | LAGYNGTIFAYGQTSSGKTHTMEG | 27 |
| consensus | L-GYNXTIFAYGQTGSGKTYTMXG | 50 |

COSTAL2 GENES AND THEIR USES

CROSS-REFERENCE TO RELATED APPLICATIONS

This application is related to provisional U.S. patent application Ser. No. 60/051,347, filed Jun. 30, 1997, which is hereby incorporated by reference herein in its entirety, and to which the present application claims benefit of priority under 35 U.S.C. §119(e).

This invention was made with support from the Howard Hughes Medical Institute. The Government may have certain rights in this invention.

BACKGROUND

Segment polarity genes were originally discovered as mutations in flies that change the pattern of body segment structures. Among the genes in this class are hedgehog, patched, and costal2. The proteins encoded by these genes form a signaling pathway that regulates key events in early development, and in adult life has been implicated in carcinogenesis. The pathway has been best studied in model organisms such as flies, but it is conserved among all animals. In this pathway, the secreted signaling protein hedgehog binds to its receptor, patched, on receiving cells. Costal2 is part of the machinery that then transduces this signal to the nucleus, resulting in changes in gene activation.

Hedgehog induces transcription of certain powerful regulatory target genes, while both patched and costal2 act in opposition to keep the target genes turned off. Other components of the pathway required for activation include the seven transmembrane protein, smoothened, the kinase fused, and cubitus inteffuptus. Experimental data suggests that hedgehog binds to patched at the cell surface, preventing patched from inactivating smoothened function. In the presence of hedgehog signal, smoothened is active, allowing it to send an activating signal to the nucleus. How hedgehog and smoothened send the activating signal to the nucleus is unknown, but genetic evidence suggests that fused and costal2 are involved. Changes in their activities are thought to allow cubitus interruptus to directly activate the transcription of hedgehog target genes.

The hedgehog signaling pathway has been implicated in several important human disease processes. For example, mutations in patched are associated with basal cell carcinomas, developmental abnormalities and brain tumors. The human homolog of cubitus interruptus, GLI, is an oncogene found in gliomas. One of the human hedgehog homologs, SHH, has also been implicated in tumorigenesis.

The characterization and identification of hedgehog signaling pathway component genes is of great interest, because of their involvement in the control of cellular differentiation and growth regulation.

RELEVANT LITERATURE

The interaction of patched (PTCH) and hedgehog is described in Chen and Struhl (1996) Cell 87: 553–563. The role of PTCH in sporadic basal cell carcinomas is described in Gailani et al. (1996) Nature Genet. 14:78–81; Hahn et al. (1996) Cell 85: 841–851; and Johnson et al. (1996) Science 272:1668–1671. Evidence that PTCH is a receptor for sonic hedgehog (SHH) is presented in Marigo et al. (1996) Nature 384:176–179; and Stone et al. (1996) Nature 384:129–134.

Cloning of SHH and IHH is described in Marigo et al. (1995) Genomics 28:44–51. The function of SHH is explored in Chiang et al. (1996) Nature 383:407–413; and Ericson et al. (1996) Cell 87:661–673.

The regulation of transcription by cubitus intemiptus is described in Von Ohlen et al. (1997) P.N.A.S. 94:2404–2409; Hepker et al. (1997) Development 124:549–558; Alexandre et al. (1996) Genes Dev. 10:2003–2013; and Dominguez et al. (1996) Science 272:1621–1625.

The first description of costal was published by Whittle (1974) Heredity 33:139. The interaction of costal2 with fused is described in Preat et al. (1993) Genetics 135:1047–1062. Genetic analysis of the region containing the Drosophila costal2 gene is found in Heitzler et al. (1993) Genetics 135:105–115.

Kinesin-like proteins are thought to be motors that bind to microtubules and use ATP to move along them like trains on tracks. Different members of the family are believed to transport different cargos. Kinesins are structurally related to myosin, even though myosin motors (which power muscle) move on actin rather than tubulin tracks, Kull et al. (1996) Nature 380:550–555. Kinesins can move toward the positive or the negative terminus of microtubules, and some act to cross-link two or more microtubules. A review of kinesins may be found in Goldstein et al. (1993) Annu. Rev. Genet. 27:319–351. The interaction between kinesins and microtubules is explored in Tucker and Goldstein (1997) J Biol Chem 272:9481–9488.

SUMMARY OF THE INVENTION

Isolated nucleotide compositions and sequences are provided for costal2 (cos2) genes. The cos2 nucleic acid compositions find use in identifying homologous or related genes; in producing compositions that modulate the expression or function of its encoded protein, Cos2; for gene therapy; mapping functional regions of the protein; and in studying associated physiological pathways. In addition, modulation of the gene activity in vivo is used for prophylactic and therapeutic purposes, such as treatment of cancer, identification of cell type based on expression, and the like.

Cos2 encodes a kinesin-related protein that accumulates preferentially in cells capable of responding to Hh. Cos2 is cytoplasmic and binds both to microtubules and to the gene products of fused (fu), and cubitus interruptus (Ci), suggesting that Cos2 directly controls the activity of Ci. Cos2 plays a novel role for kinesin-related proteins in regulating signal transduction. The cos2 protein is useful as an immunogen for producing specific antibodies, in screening for biologically active agents that act in the hedgehog signaling pathway and for therapeutic and prophylactic purposes.

BRIEF DESCRIPTION OF THE DRAWINGS

FIG. 2A shows features in the sequence of cos2.

FIG. 2B is a diagram of the predicted two structure of cos2.

FIG. 2C is an alignment of cos2 and other kinesin proteins SEQ ID NOs:2–10.

DESCRIPTION OF THE SPECIFIC EMBODIMENTS

Figure 1A:
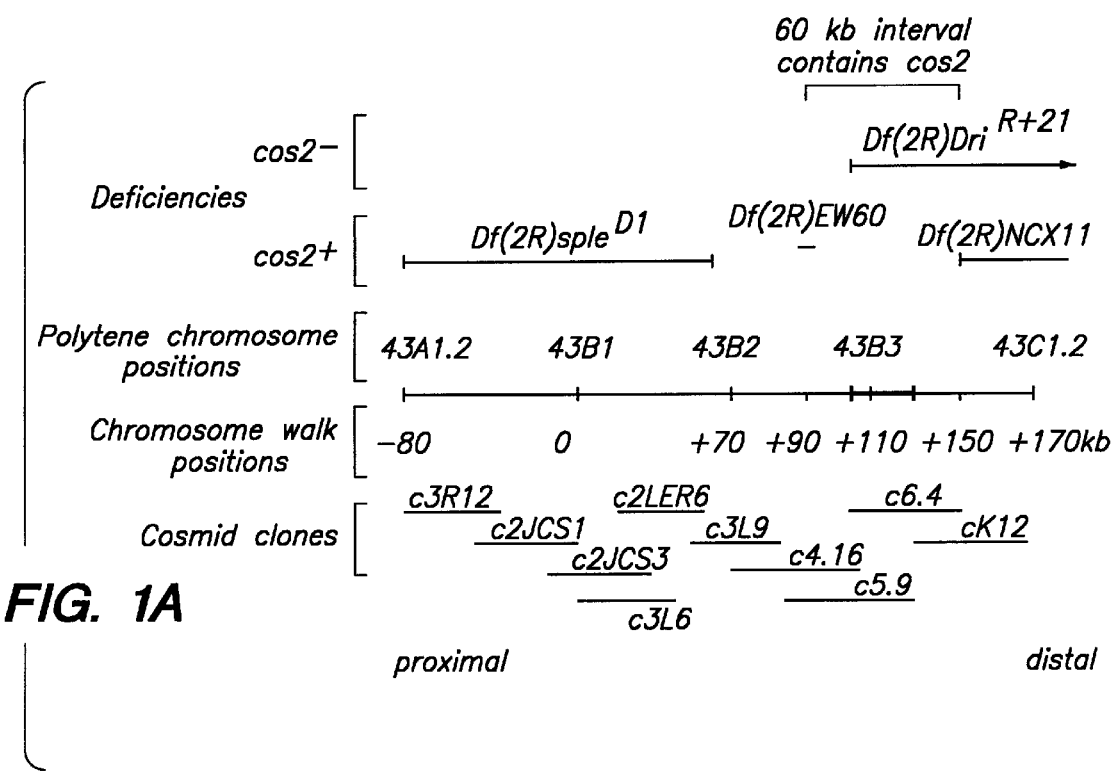
FIGS. 1A and 1B illustrate genetic maps in the cos2 region.
Figure 1B:
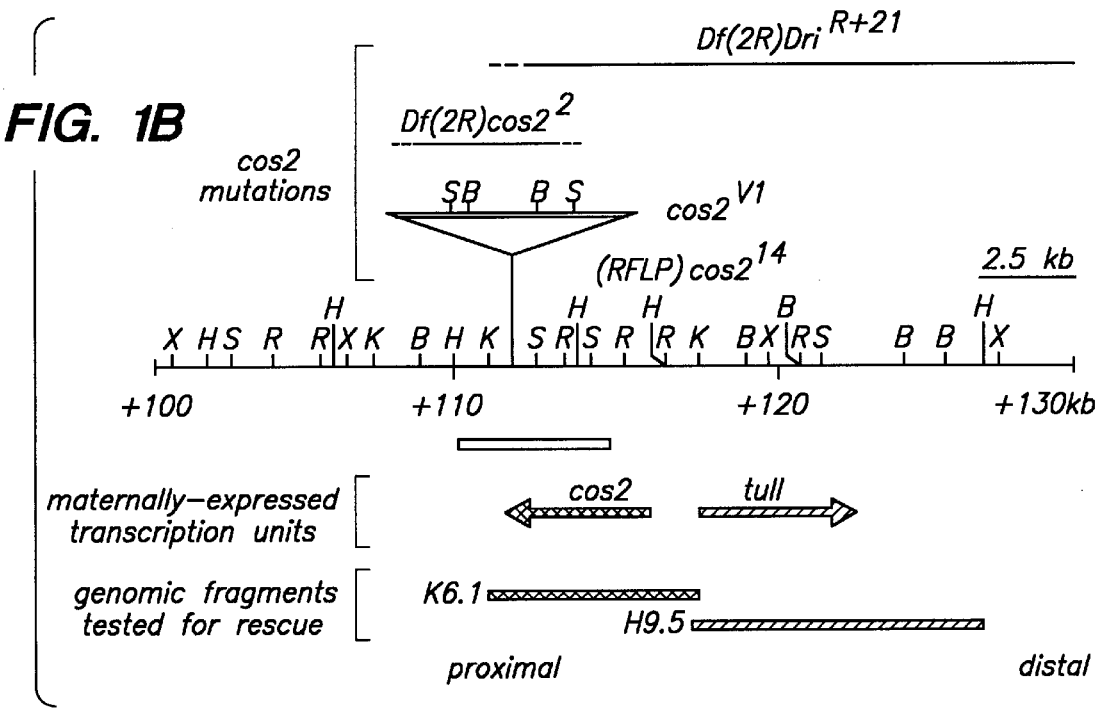

Nucleic acid compositions encoding costal2 (cos2) are provided. They are used in identifying homologous or related genes; in producing compositions that modulate the expression or function of its encoded protein; for gene therapy; mapping functional regions of the protein; and in studying associated physiological pathways. The cos2 gene product is a member of the kinesin superfamily. It directly binds to microtubules in the cytoplasm, and also binds to Ci, suggesting regulation of expression through the sequestration and/or translocation of a transcription factor.

Modulation of Cos2 gene activity in vivo is used for prophylactic and therapeutic purposes, such as treatment of cancer, investigation of hedgehog signaling pathway function, identification of cell type based on expression, and the like. The protein is useful as an immunogen for producing specific antibodies, in screening for biologically active agents that act in the hedgehog signaling pathway and for therapeutic and prophylactic purposes.

Characterization of Cos2

Cos2 is widely expressed, typically in cells that also express patched. The Drosophila gene sequence is provided as SEQ ID NO:1, the encoded polypeptide product as SEQ ID NO:2. The gene product acts to repress expression of hedgehog target genes, which include patched, members of the transforming growth factor β and Wnt gene families. The human gene is predicted to be a tumor suppressor, based on functional similarity to patched. Cos2 is also involved in many events in normal development, including formation of the neurons that are depleted in Parkinson's disease, formation of normal limbs and musculature, signaling in gut development, chondrogenesis and proper development of the brain.

Two proteins, the serine/threonine kinase, fused (Fu) and the zinc finger protein, cubitus interruptus (Ci), are required for transmitting the Hh signal. Ci has homology to the Gli family of transcription factors in vertebrates and is proposed to control directly the transcription of Hh target genes. In extracts of Drosophila embryos, Fu and Ci are found associated with the kinesin-related protein, costal-2 (Cos-2) as part of a high molecular weight complex. Cos-2, like Ptc, functions as a negative regulator of Hh signaling and can bind to microtubules. Cos-2 may inhibit Hh signaling by sequestering Ci in the cytosol to prevent it from activating gene expression. Both Cos-2 and Fu become phosphorylated in response to Hh which suggests that the activities of these proteins are modulated post-transcriptionally.

Many components of the hedgehog signaling pathway have been identified and characterized, including the following:

| Drosophila gene | Human homolog | Genbank accession no. human gene |
| --- | --- | --- |
| patched (ptch) | PTCH | U59464 |
| hedgehog (hh) | SHH | L38518 |
|  | IHH | L38517 |
|  | DHH | U59748 |
| cubitus interruptus (ci) | GLI | X07384 |
| fused (fu) | serine threonine kinase | — |
| smoothened (smo) | SMO | U84401 |
| wingless (wg) | WNT gene family | numerous |
| Protein Kinase A | PKA | numerous |
| decapentaplegic (dpp) | TGF-β gene family | numerous |

The availability of isolated genes and gene products in this pathway allows the in vitro reconstruction of the pathway and its regulation using human, mouse, or Drosophila molecules, or a combination thereof.

Identification of Cos2 Sequences

Homologs of cos2 are identified by any of a number of methods. A fragment of the Drosophila cDNA may be used as a hybridization probe against a cDNA library from the target organism of interest, where low stringency conditions are used. The probe may be a large fragment, or one or more short degenerate primers. The binding of cos2 to Ci and to microtubules can be exploited in various binding assays, e.g. yeast 2-hybrid system, etc., to identify nucleic acids encoding cos2. A mammalian homolog of Ci, i.e. one of the GLI family of transcription factors, may be used to identify human and other genes using such a binding assay.

In an alternative approach, conserved regions between different invertebrate homologs of cos2 may be used to design primers useful for hybridizing to vertebrate, especially mammalian homologs. Such sequences are selected from regions that are not likely to diverge over evolutionary time and are of low degeneracy. The complementary binding sequence will usually be at least 14 nucleotides, preferably at least about 17 nucleotides and usually not more than about 30 nucleotides. Conveniently, amplification reactions are used to generate an initial probe, which can then be used to hybridize to a library; for rapid amplification of cloned ends (RACE); etc. One or more of the resulting clones may then be used to rescreen the library to obtain an extended sequence, up to and including the entire coding region, as well as the non-coding 5'- and 3'-sequences. As appropriate, one may sequence all or a portion of the resulting cDNA coding sequence. The source of mRNA for a cDNA library will use cells where patched is known to be expressed, for example embryonic limb bud tissue.

Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity may be determined by hybridization under stringent conditions, for example, at 50° C. or higher and 0.1×SSC (9 mM saline/0.9 mM sodium citrate). By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, nematodes, etc.

Between mammalian species, e.g. human and mouse, homologs have substantial sequence similarity, i.e. at least 75% sequence identity between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) *J Mol Biol* 215:403–10. The sequences provided herein are utilized for recognizing cos2 related and homologous proteins in database searches.

Cos2 Nucleic Acid Compositions

Nucleic acids encoding cos2 may be cDNA or genomic DNA or a fragment thereof. The term "cos2 gene" shall be intended to mean the open reading frame encoding specific cos2 polypeptides, introns, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into the host.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, removed by nuclear RNA splicing, to create a continuous open reading frame encoding a cos2 protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression.

The sequence of the 5' flanking region may be utilized for promoter elements, including enhancer binding sites, that provide for developmental regulation in tissues where cos2 is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al. (1995) *Mol Med* 1: 194–205; Mortlock et al. (1996) *Genome Res.* 6: 327–33; and Joulin and Richard-Foy (1995) *Eur J Biochem* 232: 620–626.

The regulatory sequences may be used to identify cis acting sequences required for transcriptional or translational regulation of cos2 expression, especially in different tissues or stages of development, and to identify cis acting sequences and trans acting factors that regulate or mediate cos2 expression. Such transcription or translational control regions may be operably linked to a cos2 gene in order to promote expression of wild type or altered cos2 or other proteins of interest in cultured cells, or in embryonic, fetal or adult tissues, and for gene therapy.

The nucleic acid compositions of the subject invention may encode all or a part of the subject polypeptides. Double or single stranded fragments may be obtained of the DNA sequence by chemically synthesizing oligonucleotides in accordance with conventional methods, by restriction enzyme digestion, by PCR amplification, etc. For the most part, DNA fragments will be of at least 15 nt, usually at least 18 nt, more usually at least about 50 nt. Such small DNA fragments are useful as primers for PCR, hybridization screening probes, etc. Larger DNA fragments, i.e. greater than 100 nt are useful for production of the encoded polypeptide. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

The cos2 genes are isolated and obtained in substantial purity, generally as other than an intact chromosome. Usually, the DNA will be obtained substantially free of other nucleic acid sequences that do not include a cos2 sequence or fragment thereof, generally being at least about 50%, usually at least about 90% pure and are typically "recombinant", i.e. flanked by one or more nucleotides with which it is not normally associated on a naturally occurring chromosome.

The DNA may also be used to identify expression of the gene in a biological specimen. The manner in which one probes cells for the presence of particular nucleotide sequences, as genomic DNA or RNA, is well established in the literature and does not require elaboration here. DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of cos2 gene expression in the sample.

The sequence of a cos2 gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions or deletions. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al., *Biotechniques* 14:22 (1993); Barany, *Gene* 37:111–23 (1985); Colicelli et al., *Mol Gen Genet* 199:537–9 (1985); and Prentki et al., *Gene* 29:303–13 (1984). Methods for site specific mutagenesis can be found in Sambrook et al., *Molecular Cloning: A Laboratory Manual*, CSH Press 1989, pp. 15.3–15.108; Weiner et al., *Gene* 126:35–41 (1993); Sayers et al., *Biotechniques* 13:592–6 (1992); Jones and Winistorfer, *Biotechniques* 12:528–30 (1992); Barton et al., *Nucleic Acids Res* 18:7349–55 (1990); Marotti and Tomich, *Gene Anal Tech* 6:67–70 (1989); and Zhu, *Anal Biochem* 177:120–4 (1989). Such mutated genes may be used to study structure-function relationships of cos2, or to alter properties of the protein that affect its function or regulation.

Cos2 Polypeptides

The subject gene may be employed for producing all or portions of cos2 polypeptides. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a cos2 gene, or may be derived from exogenous sources.

The peptide may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the cos2 gene in eukaryotic cells, where the cos2 protein will benefit from native folding and post-translational modifications. Small peptides can also be synthesized in the laboratory. Peptides that are subsets of the complete cos2 sequence, e.g. peptides of at least about 8 amino acids in length, usually at least about 12 amino acids in length, and may be as many as about 20 amino acids in length, up to substantially the length of the intact protein, may be used to identify and investigate parts of the protein important for function, such as the Ci or microtubule binding domains, the kinesin-like "motor", or to raise antibodies directed against these regions.

With the availability of the protein or fragments thereof in large amounts, by employing an expression host, the protein may be isolated and purified in accordance with conventional ways. A lysate may be prepared of the expression host and the lysate purified using HPLC, exclusion chromatography, gel electrophoresis, affinity chromatography, or other purification technique. The purified protein will generally be at least about 80% pure, preferably at least about 90% pure, and may be up to and including 100% pure. Pure is intended to mean free of other proteins, as well as cellular debris.

The expressed cos2 polypeptides are used forthe production of antibodies, where short fragments provide for antibodies specific for the particular polypeptide, and larger fragments or the entire protein allow for the production of antibodies over the surface of the polypeptide. Antibodies may be raised to the wild-type or variant forms of cos2. Antibodies may be raised to isolated peptides corresponding to these domains, or to the native protein.

Antibodies are prepared in accordance with conventional ways, where the expressed polypeptide or protein is used as an immunogen, by itself or conjugated to known immunogenic carriers, e.g. KLH, pre-S HBsAg, other viral or eukaryotic proteins, or the like. Various adjuvants may be employed, with a series of injections, as appropriate. For monoclonal antibodies, after one or more booster injections, the spleen is isolated, the lymphocytes immortalized by cell fusion, and then screened for high affinity antibody binding. The immortalized cells, i.e. hybridomas, producing the desired antibodies may then be expanded. For further description, see *Monoclonal Antibodies: A Laboratory Manual*, Harlow and Lane eds., Cold Spring Harbor Laboratories, Cold Spring Harbor, N.Y., 1988. If desired, the mRNA encoding the heavy and light chains may be isolated and mutagenized by cloning in *E. coli*, and the heavy and light chains mixed to further enhance the affinity of the antibody. Alternatives to in vivo immunization as a method of raising antibodies include binding to phage "display" libraries, usually in conjunction with in vitro affinity maturation.

Diagnostic Uses

The subject nucleic acid and/or polypeptide compositions may be used to analyze a patient sample for the presence of polymorphisms associated with a disease state or genetic predisposition to a disease state. Biochemical studies may be performed to determine whether a sequence polymorphism in a cos2 coding region or control regions is associated with disease, particularly developmental abnormalities, cancers, e.g. basal cell carcinoma, glioma, medulloblastoma, meningioma, breast carcinoma, etc. Disease associated polymorphisms may include mutations that alter expression level, that affect the binding activity of the protein to Ci or to microtubules, that alter the subcellular localization of cos2, etc.

Changes in the promoter or enhancer sequence that may affect expression levels of cos2 can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express cos2 may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985) *Science* 239:487, and a review of techniques may be found in Sambrook, et al. *Molecular Cloning: A Laboratory Manual*, CSH Press 1989, pp.14.2–14.33. Alternatively, various methods are known in the art that utilize oligonucleotide ligation as a means of detecting polymorphisms, for examples see Riley et al. (1990) N.A.R. 18:2887–2890; and Delahunty et al. (1996) *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine(TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type cos2 sequence. Hybridization with the variant sequence may also be used to determine its presence, by Southern blots, dot blots, etc. The hybridization pattern of a control and variant sequence to an array of oligonucleotide probes immobilised on a solid support, as described in U.S. Pat. No. 5,445,934, or in WO95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoreticmobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in cos2 may be based on the functional or antigenic characteristics of the protein. Protein truncation assays are useful in detecting deletions that may affect the biological activity of the protein. Various immunoassays designed to detect polymorphisms in cos2 proteins may be used in screening. Where many diverse genetic mutations lead to a particular disease phenotype, functional protein assays have proven to be effective screening tools. The activity of the encoded cos2 protein in regulation of Ci (GLI), transport and/or sequestration of transcription factors, etc., may be determined by comparison with the wild-type protein.

Antibodies specific for a cos2 may be used in staining or in immunoassays. Samples, as used herein, include biological fluids such as semen, blood, cerebrospinal fluid, tears, saliva, lymph, dialysis fluid and the like; organ or tissue culture derived fluids; and fluids extracted from physiological tissues. Also included in the term are derivatives and fractions of such fluids. The cells may be dissociated, in the case of solid tissues, or tissue sections may be analyzed. Alternatively a lysate of the cells may be prepared.

Diagnosis may be performed by a number of methods to determine the absence or presence or altered amounts of normal or abnormal cos2 in patient cells. For example, detection may utilize staining of cells or histological sections, performed in accordance with conventional methods. Cells are permeabilized to stain cytoplasmic molecules. The antibodies of interest are added to the cell sample, and incubated for a period of time sufficientto allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g. flourescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Modulation of Gene Expression

The cos2 genes, gene fragments, or the encoded protein or protein fragments are useful in gene therapy to treat disorders associated with cos2 defects. Expression vectors may be used to introducethe cos2 gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or cos2 protein may be introduced into tissues or host cells by any number of routes, including viral infection, microinjection, or fusion of vesicles. Jet injection may also be used for intramuscular administration, as described by Furth et al. (1992) Anal Biochem 205:365–368. The DNA may be coated onto gold microparticles, and delivered intradermally by a particle bombardment device, or "gene gun" as described in the literature (see, for example, Tang et al. (1992) Nature 356:152–154), where gold microprojectiles are coated with the cos2 or DNA, then bombarded into skin cells.

Antisense molecules can be used to down-regulate expression of cos2 in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996) Nature Biotechnology 14:840–844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate,3'-S-5'-O-phosphorothioate,3'-CH2-5'-O-phosphonate and 3'-NH-5'-O-phosphoroamidate. Peptide nucleic acids replace the entire ribose phosphodiesterbackbone with a peptide linkage. Sugar modifications are also used to enhance stability and affinity. The a-anomer of deoxyribose may be used, where the base is inverted with respect to the natural P-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5- propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995) *Nucl. Acids Res* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995) *Appl Biochem Biotechnol* 54:43–56.

Genetically Altered Cell or Animal Models for Costal2 Function

The subject nucleic acids can be used to generate transgenic animals or site specific gene modifications in cell lines. Transgenic animals may be made through homologous recombination, where the normal costal2 locus is altered. Alternatively, a nucleic acid construct is randomly integrated into the genome. Vectors for stable integration include plasmids, retroviruses and other animal viruses, YACs, and the like.

The modified cells or animals are useful in the study of costal2 function and regulation. For example, a series of small deletions and/or substitutions may be made in the costal2 gene to determine the role of different exons in oncogenesis, signal transduction, etc. Of interest are the use of cos2 to construct transgenic animal models for cancer, where expression of cos2 is specifically reduced or absent, e.g. in skin cells, brain cells, etc. For models of skin abnormalities, one may use a skin-specific promoter to drive expression of the transgene, or other inducible promoter that can be regulated in the animal model. Such promoters include keratin gene promoters. Specific constructs of interest include anti-sense cos2, which will block cos2 expression, expression of dominant negative cos2 mutations, and over-expression of HH genes. A detectable marker, such as lac Z may be introduced into the costal2 locus, where upregulation of costal2 expression will result in an easily detected change in phenotype.

One may also provide for expression of the costal2 gene or variants thereof in cells or tissues where it is not normally expressed or at abnormal times of development. Thus, mouse models of spina bifida or abnormal motor neuron differentiation in the developing spinal cord are made available. In addition, by providing expression of cos2 protein in cells in which it is not normally produced, one can induce changes in cell behavior, e.g. through cos2 mediated transcription modulation. Production of specific neuron types, such as dopaminergicor serotonergic neurons, may be accomplished by altering cos2 function.

Hh genes, which oppose cos2 function, have been implicated in spermatogenesis and oogenesis. Manipulation of cos2 may therefore lead to new treatments for infertility or new types of contraception. Inactivation of one allele of patched in mice allows them to grow to abnormally large size; overproduction of patched causes mice to be small. The functional relationship between cos2 and patched means that cos2 can be manipulated to control growth.

DNA constructs for homologous recombination will comprise at least a portion of the costal2 gene with the desired genetic modification, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keyed et al. (1990) *Methods in Enzymology* 185:527–537.

For embryonic stem (ES) cells, an ES cell line may be employed, or embryonic cells may be obtained freshly from a host, e.g. mouse, rat, guinea pig, etc. Such cells are grown on an appropriate fibroblast-feederlayer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on GLI transcriptional activation, developmental abnormalities, etc.

Mice and humans heterozygous for patched mutations have numerous developmental defects and a high incidence of a variety of cancers. cos2 heterozygotes are useful animal models for human disease. By intervening in intracellular rather than membrane signaling events, different drugs may be discovered using cos2 vs. patched models.

In Vitro Models for Costal2 Function

The availability of a number of components in the hedgehog signaling pathway, including SHH, PTCH, Ci (GLI), FU, PKA and COS2, allows in vitro reconstruction of the pathway. Two or more of the components may be combined in vitro, and the behavior assessed in terms of activation of transcription of specific target sequences; modification of protein components, e.g. proteolytic processing, phosphorylation, methylation, etc.; ability of different protein components to bind to each other; utilization of ATP, GTP, etc. The binding and translocation along microtubules is of interest for cos2 function. The components may be modified by sequence deletion, substitution, etc. to determine the functional role of specific domains.

Drug screening may be performed using an in vitro model, a genetically altered cell or animal, or purified costal2 protein. One can identify ligands or substrates that bind to, modulate or mimic the action of costal2. Areas of investigation include the development of cancer treatments, wound healing, adverse effects of aging, metastasis, etc. The functional similarity of costal2 and patched gene products suggests that agents that modulate each of these protein activities will have similar activity, but different structures.

Drug screening identifies agents that provide a replacement for Cos2 function in abnormal cells. Agents that mimic its function, in terms of transcriptional down-regulation, etc., are predicted to inhibit the process of oncogenesis. Conversely, agents that reverse Cos2 function may stimulate controlled growth and healing. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The purified protein may also be used for determination of three-dimensional crystal structure, which can be used for modeling intermolecular interactions, such as microtubule or Ci binding, potential kinesin motor activity, etc.

The term "agent" as used herein describes any molecule, e.g. protein or pharmaceutical, with the capability of altering or mimicking the physiological function of costal2. Generally a plurality of assay mixtures are run in parallel with different agent concentrationsto obtain a differential response to the various concentrations. Typically, one of these concentrations serves as a negative control, i.e. at zero concentration or below the level of detection.

Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Where the screening assay is a binding assay, one or more of the molecules may be joined to a label, where the label can directly or indirectly provide a detectable signal. Various labels include radioisotopes, fluorescers, chemiluminescers, enzymes, specific binding molecules, particles, e.g. magnetic particles, and the like. Specific binding molecules include pairs, such as biotin and streptavidin, digoxin and antidigoxin etc. For the specific binding members, the complementary member would normally be labeled with a molecule that provides for detection, in accordance with known procedures.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components are added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

Other assays of interest detect agents that mimic costal2 function, such as repression of target gene transcription, binding properties, etc. For example, an expression construct comprising a costal2 gene may be introduced into a cell line under conditions that allow expression. The level of costal2 activity is determined by a functional assay, as previously described. In one screening assay, candidate agents are added in combination with Ci protein, and the ability to prevent Ci activation is detected. In another assay, the ability of candidate agents to enhance Cos2 function is determined. Alternatively, candidate agents are added to a cell that lacks functional Cos2, and screened for the ability to reproduce Cos2 in a functional assay.

The interaction between cos2 and microtubules is of interest for drug screening. Such assays may determine the effect of agents on cos2 function, or investigate the specific binding parameters of cos2 for microtubules. The main component of microtubules is tubulin protein. Soluble tubulin exists in the form of dimers of $\alpha$ and $\beta$ tubulin. The dimers consist of a pair of $\alpha$ and $\beta$ tubulin proteins, which are tightly bound. These soluble dimers reversibly assemble in large numbers and form microtubules. Normal cellular function requires that tubulin may exist both in the soluble and polymerized forms, depending on the needs of the cells. Each of the α and β tubulin proteins exist under different forms, designated as isotypes. Isotypes differ among themselves by slight variations in their amino acid sequences, although they are identical for more than 90% of their sequence. These isotypes are present in various tissues at very different levels, some of the isotypes being expressed predominantly or exclusively in certain tissues.

A number of agents are known that affect microtubules. Colchicine binds stochiometricallyto soluble tubulin dimers, slowing or preventing their incorporation into microtubules. Vinca alkaloids (vinblastine, vincristine and vinorelbine) act similarly to colchicine but at a differenttubulin binding site. Taxanes (paclitaxel and docetaxel) have the opposite effect, and enhance the polymerization of tubulin. These drugs are predicted to affect cos2 function.

The compounds having the desired pharmacological activity may be administered in a physiologically acceptable carrier to a host for treatment of cancer, developmental abnormalities attributableto a defect in costal2 function, etc. The compounds may also be used to enhance costal2 function in wound healing, aging, etc. The inhibitory agents may be administered in a variety of ways, orally, topically, parenterally e.g. subcutaneously, intraperitoneally, by viral infection, intravascularly, etc. Topical treatments are of particular interest. Depending upon the manner of introduction, the compounds may be formulated in a variety of ways. The concentration of therapeutically active compound in the formulation may vary from about 0.1–100 wt. %.

The pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions containing the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Molecular cloning and hybridizations. Molecular biology techniques were carried out according to Sambrook et al. (1989). The cos2 chromosome walk was initiated with a genomic clone (λB47) and using a cosmid library made from an isogenic fly stock (iso-1). The progress of the walk and positions of deficiencies were determined by in situ hybridization of biotin-labeled DNA fragments to polytene chromosomes. Overlapping iso-1 genomic λ phage clones lying between $Df(2R)sple^{D1}$ and Df(2R)NCX11 were isolated, and positions of cos2 mutations were determined using blots of cos2 mutant genomic DNA. From 38 cos2 cDNA clones recovered from a λgt10, 0–3 hour embryonic, cDNA library and a plasmid-based imaginal disc cDNA library two approximately full-length clones, D12 and D13, were found and sequenced. In situ hybridization of riboprobes to embryos and imaginal discs was carried out as described (Mathies et al. (1994) Development 120, 2799–2809).

Germ line transformations. The 6.1 kb KpnI (K6.1) and 9.5 kb HindIII (H9.5) genomic fragments were subcloned into pCaSpeR4. Transgenic flies were made according to Spradling and Rubin (1982) Science 218, 341–7, using $w^{1118}$ embryos as recipients. Seven independent K6.1 inserts and eight independent H9.5 inserts were recovered.

Antibody preparation and immunoblotting. Affinity-purified rat polyclonal antisera were prepared to two parts of Cos2. A 1.5 kb SacI-EcoRI (SR1.5) fragment, including the putative motor domain, and a 0.8 kb EcoRI (R0.8) fragment, including the N-terminal 19 heptad-repeats, were each subcloned into two different plasmid expression vectors, pATH10, Rimm and Pollard (1989) Gene 75, 323–327 and pGEX-2T (128/129). The pATH10 clones create E. coli TrpE-Cos2 fusion proteins which were used as immunogens. Each TrpE-Cos2 fusion protein was purified from the BL21 pLysS cell lysates as inclusion bodies, cut from SDS gels, and injected into rats. The pGEX-2T (128/129) clones create Glutathione-S-Transferase (GST)-Cos2 fusion proteins, which were used to affinity purify the rat antisera. Soluble GST-Cos2 fusion proteins were purified from BL21 pLysS cells using glutathione-agarose beads and coupled to AminoLink® Plus chromatography columns (Pierce). Antibodies were eluted from columns with 4.5 M $MgCl_2$ and dialyzed against 50 mM HEPES pH 7.5, 150 mM NaCl, 1 mM EDTA and 0.01% $NaN_3$.

Immunoblots were carried out as described (Harlow and Lane, 1988 Antibodies: A Laboratory Manual, Cold Spring Harbor Laboratory). After 7.5% SDS-PAGE, proteins were transferred to Protran membrane (Schleicher and Schuell), and membranes were blocked with 5% nonfat dry milk for 2–6 hrs. Antibodies used are as follows: Cos2, rat polyclonal antisera (1:50); Ci, rat monoclonal (1:5); α-Tubulin, mouse monoclonal (1:100); En, mouse monoclonal (1:500); DmKhc, DK410-7.1 mouse monoclonal (1:250); Sgg/Zw3, rabbit polyclonal (1:500); and all Horseradish Peroxidase (HRP) conjugated secondary antibodies (1:20,000, Jackson ImmunoResearch Labs). HRP was detected with Chemiluminescence reagent (NEN).

Anterior or posterior fragments of wing discs were dissected from third instar larvae and transferred to 40 mM Tris pH 7.2, 250 mM NaCl, 5 mM EDTA, and 0.05% NP-40 on ice, 0.5 fragments/μl. Fragments stored at −80° C. were thawed and homogenized. Approximately 70 anterior and posterior disc fragment equivalents were analyzed by immunoblotting.

Protein detection in embryos and discs. Washed and dechorionated embryos were fixed with either heat and methanol, methanol, or formaldehyde. After fixation embryos were stored either at −20° C. in methanol or taken through a rehydration series to prepare embryos for indirect immunofluorescence. Third instar larval imaginal discs were prepared for indirect immunofluorescence as described by (Johnson et al. (1995) Development 121, 4161–4170). Samples were mounted in Vectashield™ H-1000 (Vector Laboratories Inc.) and examined by confocal microscopy. Antibodies used are as follows: Cos2, rat polyclonal antisera (1:5); α-Tubulin, mouse monoclonal (1:25); Lamin, mouse monoclonal (1:40); β-gal, rabbit polyclonal (1:100, Cappel); and all fluorescent secondary antibodies (1:200, Jackson immunoResearch Labs).

Microtubule-binding assays. This assay was carried out according to Kellogg et al. (1989) J. Cell Biol. 109, 2977–2991, with some modifications. Briefly, 16 g of 2–10 hour Canton S embryos were homogenized in 32 mls of C buffer (50 mM HEPES, pH 7.6, 1 mM $MgCl_2$, 1 mM EGTA and protease inhibitors (0.5 mM DTT, 1.74 μg/ml PMSF, 1 mM benzamidine, 2 μg/ml aprotinin, 1 μg/ml leupeptin, 1 μg/ml pepstatin, all from Sigma) on ice. A supernatant (S100) was prepared and five 5 ml aliquots were made. One aliquot received 40 μM taxol (Sigma) and 1 mM GTP (binding), three aliquots received 40 μM taxol, 1 mM GTP, 80 U/ml apyrase (Sigma), and 0.5 mM AMP-PNP (Boehringer-Mannheim) (binding, lanes 6 and 7, and extractions), one was not supplemented (–taxol). Aliquots were incubated at 25° C. for 20' and then on ice for 10'. 4.5 mls of each sample was layered over a 10% sucrose cushion and centrifuged at 48,000×g for 30' at 4° C. For the –taxol and both binding samples, supernatants were saved and pellets were washed and resuspended in 4.5 mls of CX buffer (C buffer supplemented with 10% glycerol, 25 mM KCl and protease inhibitors). For the extraction samples, pellets were resuspended in 1 ml of CX buffer (supplemented with 40 μM taxol, 1 mM GTP and either 5 mM Mg-ATP or 5 mM Mg-ATP and 0.5 M KCl) and incubated on ice for 10 hours before centrifugation as before. The resulting supernatants were saved and pellets were resuspended in 1 ml of CX buffer. 15 μl of each sample (in 1×sample buffer) was separated by SDS-PAGE and immunoblotted.

Chromatography. A Sepharose 4B (Pharmacia) column (48.5 cm×1.77 $cm^2$ equaling a bed volume ($V_t$) of 86 ml, void volume ($V_o$)=28.5 ml) was calibrated with protein standards (Pharmacia) and operated at a pressure head of 64 cm with a flow rate of 17.5 ml/hr. Embryos were homogenized in TNE buffer (40 mM Tris pH 7.2, 250 mM NaCl, 0.5 mM EDTA, 10% glycerol, 0.05% NP-40 and 1 μg/ml nocodazole)+proteinase inhibitors (previously listed), a S100 protein extract was prepared as above and dialyzed against column running buffer overnight at 4° C. The S100 was recentrifuged at 100,000×g for 30' at 4° C. The total protein concentration of the resulting S100 was determined (34 mg/ml) and 250 μl (8.5 mg) was loaded onto the column. Column runs were monitored by a UV-spectophotometer at O.D. $A_{280}$ and 1.5 ml fractions were collected. Proteins were precipitated with acetone and analyzed by immunoblot.

Coimmunoprecipitation. An embryonic extract (S43) prepared in TNE buffer+proteinase inhibitors was preincubated with Protein G Sepharose beads (Pharmacia) for 30' at 4° C. with rocking. Beads were pelleted in a microfuge (30"), and the pellet saved for immunoblotting. 100 μl aliquots of the supernatant were transferred to fresh tubes and supplemented with 1 μl of rat polyclonal Cos2 antisera, 1 μl of rabbit polyclonal Ci antisera, or 1 μl of preimmune sera, and then rocked at 4° C. for 30'. Protein G Sepharose beads were added and samples rocked for 2 h at 4° C. Beads pelleted as before were washed 3 times with TNE buffer. Washed beads were centrifuged and pellets and supernatants were examined by immunoblotting.

Somatic clones. cos2 mutant clones were made with $cos2^{W1}$. Both P[$w^+$; FRT]$^{G13}$ $cos2^{W1}$/CyO flies and P[$w^+$; FRT]$^{G13}$ P[hsp70-Myc](G13-πM) flies were crossed separately with yw P[$ry^+$;FLP]$^{12}$; CyO/Sco flies. yw P[$ry^+$; FLP]$^{12}$; P[$w^+$; FRT]$^{G13}$ $cos2^{W1}$/CyO and yw P[$ry^+$; FLP]$^{12}$; G13-πM/CyO siblings were crossed and after 2 days adults were transferred to fresh vials. Larvae were heat-shocked on days 2, 3, and 4 for one hour at 37° C. Imaginal discs were dissected from third instar larvae 30' after a fourth one-hour heat shock. Discs were incubated with monoclonal antibodies 9E10 anti-Myc (Sigma, 1:500) and 2A1 anti-Ci (1:5) and prepared for indirect immunofluorescence.

K6.1 was tested for the ability to rescue $cos2^2$/$cos2^{12}$ embryonic lethality. $cos2^2$ behaves like a null allele and $cos2^{12}$ is a strong loss of function allele. (Upper cross) $cos2^2$ and $cos2^{12}$ fail to complement one another. $cos2^-$/CyO represents both $cos2^2$/CyO and $cos2^{12}$/CyO genotypes. (Lower cross) $cos2^2$/CyO virgin females that possess an insertion of K6.1(2) were crossed to $cos2^{12}$/CyO males lacking K6.1(2). All flies are white (w). K6.1(2) carries mini-w and the orange eye color it confers was used to identify the K6.1(2) bearing chromosome.

Results

Molecular identification of cos2. cos2 is located on the right arm of the second chromosome within polytene interval 43B2; 43C1.2. A chromosome walk was initiated from a chromosome position proximal to cos2 at 43B1 (FIG. 1A). Df(2R)sple$^{D1}$ (43A1.2;43B2) and Df(2R)NCX11 (43C1.2; 44C1.2) complement cos2 mutations and bracket the cos2 locus. The chromosome walk spans the distance between their adjacent deficiency endpoints at positions $^+$70 and $^+$150 kb. Df(2R)EW60 complements cos2 mutations and removes DNA centered over position $^+$90 (FIG. 1A). Df(2R)Drf$^{R+21}$ fails to complement cos2 mutations and lies distal of Df(2R) EW60. Together Df(2R)EW60 and Df(2R)NCX11 limit the DNA interval containing cos2 to 60 kb (FIG. 1A, horizontal bracket).

In FIG. 1(A), the thick horizontal bars (top) indicate the positions of four deficiencies relative to polytene chromosome positions and corresponding chromosome walk positions (middle). Thin horizontal bars (bottom) indicate the positions of overlapping cosmid clones. cos2 lies within a 60 kb interval between Df(2R)EW60 and Df(2R)NCX11. The thick line within this interval, overlapping 43B3 (+110), is enlarged in 1(B). 1(B) Four cos2 mutations are close to two maternally expressed transcription units. Thick horizontal bars above the restriction map indicate positions of cos2 mutations. Hatching indicates uncertain deficiency endpoints. Df(2R)Drl$^{R+21}$ and Df(2R)cos2$^2$ define a 5 kb interval (open bar) containing a portion of cos2. $cos2^{V1}$ is an insertion and $cos2^{14}$ is associated with RFLPs within a 1.9 kb EcoRI fragment. Thick arrows below the restriction endonuclease map indicate the positions and directions of transcription of cos2 and tull. A 6.1 KpnI genomic fragment (K6.1, solid bar) fully rescues cos2 embryonic lethality to adulthood. A 9.5 kb HindIII genomic fragment (H9.5, hatched bar) fails to rescue cos2 embryonic lethality. B=BamHI, H=HindIII, K=KpnI, R=EcoRI, S=SalI and X=XbaI. (C) A blot containing total RNA from different embryonic stages and third instar larvae was hybridized to radioactive cos2 and rp49 probes. The cos2 probe reveals a single 4.9 kb transcript. rp49 serves as a loading control.

An analysis of the 60 kb region with genomic DNA blots reveals restriction fragment length polymorphisms (RFLPs) for several cos2 mutations and places part or all of cos2 within a 5 kb interval of DNA. Df(2R)cos2$^2$ behaves as an amorphic allele of cos2 and has a 6.5 kb DNA deletion between positions $^+$108 and $^+$115. Df(2R)Drf$^{R+21}$ has a proximal endpointwhich lies within the Df(2R)cos2$^2$ deletion, between $^+$110 and $^+$111. Therefore, part or all of cos2 must lie within the 5 kb region of their overlap, between $^+$110 and $^+$115. Two additional cos2 alleles map to this region. $cos2^{V1}$ is a viable allele that displays adult pattern duplications in the presence of semi-dominant alleles of Cos1. cos2$^{V1}$ is associated with a 9 kb insertion at position $^{+}$112. In addition, cos2$^{14}$, a strong hypomorphic allele, is associated with RFLPs between $^{+}$115 and +117.

cos2 is maternally active, so cos2 mRNA is likely to be present in early embryos prior to the onset of zygotic transcription at 2.5 hours (h) after fertilization. Radioactive cDNA synthesized from 0–2 h, 4–8 h, or 8–16 h embryonic poly (A)$^{+}$ RNA was hybridized to blots containing the 60 kb cos2 region. Two contiguous SalI fragments (1.2 kb and 6.3 kb) which overlap the 5 kb cos2 region hybridize to the 0–2 h cDNA probe cDNA clones overlapping the large SalI fragment were recovered for two adjacent, divergently transcribed, maternally expressed transcription units.

To determine which transcription unit is cos2, genomic fragments containing either the proximal or distal transcription unit were tested for their ability to rescue cos2 embryonic lethality. Transgenic flies were constructed carrying either a 6.1 kb genomic KpnI fragment (K6.1) containing the proximal transcription unit or a 9.5 kb genomic HindIII fragment (H9.5) containing the distal transcription unit. A single copy of K6.1 is sufficient to rescue cos2$^{2}$/cos2$^{12}$ embryos to adulthood (Table 1). The number of cos2$^{2}$/cos2$^{12}$ adults suggests that K6.1 contains all or a substantial proportion of cos2. H9.5 does not rescue cos2 embryonic lethality.

A 4.8 kb cos2 cDNA hybridizes to a 4.9 kb transcript present at high levels during the first four hours of embryogenesis, moderate levels between four and twelve hours, and low levels for the duration of embryogenesis. The transcript is also present during the third larval instar.

TABLE 1

Rescue of cos2 Embryonic Lethality

♀ cos2$^{2}$/CyO; +/+ × cos2$^{12}$/CyO; +/+ ♂

|  | # adults |  |  |
|---|---|---|---|
| cos2$^{2}$/cos2$^{12}$ | 0 |  |  |
| cos2$^{-}$/CyO | 431 |  |  |

♀ cos2$^{2}$/CyO; K6.1/+ × cos2$^{12}$/CyO; +/+ ♂

|  | # adults | expected ratios | observed ratios |
|---|---|---|---|
| cos2$^{2}$/cos2$^{12}$; K6.1/+ | 297 | 1 | 1.0 |
| cos2$^{2}$/cos2$^{12}$; +/+ | 0 | 0 | 0 |
| cos2$^{2}$CyO; K6.1/+ | 520 | 2 | 1.7 |
| cos2$^{2}$/CyO; +/+ | 530 | 2 | 1.8 |

K6.1 was tested for the ability to rescue cos2$^{2}$/cos2$^{12}$ embryonic lethality. cos2$^{2}$ behaves like a null allele and cos2$^{12}$ is a strong loss of function allele. (Upper cross) cos2$^{2}$ and cos2$^{12}$ fail to complement one another. cos2/CyO represents both cos2$^{2}$/CyO and cos2$^{12}$/CyO genotypes. (Lower cross) cos2$^{2}$/CyO virgin females that possess an insertion of K6.1(2) were crossed to cos2$^{12}$/CyO males lacking K6.1(2). All flies are white$^{-}$ (w$^{-}$). K6.1(2) carries mini-w and the orange eye color it confers was used to identify the K6.1(2) bearing chromosome. cos2 encodes a kinesin heavy chain-related protein. The complete sequence of a 4.8 kb cDNA clone for cos2 was determined, as was all of the genomic sequence flanking the cDNA in the rescuing transgene. The cDNA sequence reveals a single large open reading frame (ORF). The putative translational start site matches the Drosophila consensus sequence well and contains codons common in other Drosophila genes. Multiple stop codons in all three reading frames are present upstream of the putative start codon. The surrounding genomic sequence contains three short ORFs which do not begin with methionine or match the usual pattern of Drosophila codon usage.

cos2 is predicted to encode a 1201 amino acid polypeptide with a molecular weight of 133 kD. The N-terminal (residues 1–450) and C-terminal (residues 1050–1201) regions are predicted to form globular structures consisting of alternating α-helices and β-sheets. The central region (residues 643–990) contains 36 heptad-repeats which are predicted to mediate the formation of a stable homodimer through a parallel coiled-coil. The sequence is shown in FIG. 2A. The N-terminus contains three putative nucleotide-binding motifs, N1 (P-loop), shaded box; N2, thick underline; and N3, dotted underline (Vale, 1996) and two putative microtubule-binding motifs (open boxes). The central portion contains 36 heptad-repeats arranged in eight clusters (thin underlining). FIG. 2(B) shows the predicted structure of Cos2. Sequence analyses predict that the N- and C-termini adopt globular conformations and that the 36 heptad-repeats mediate the formation of a homodimer by forming a parallel coiled-coil.

Cos2 is similar to members of the kinesin protein family. Over a span of 254 N-terminal amino acids (residues 136–389) Cos2 is 25%–30% identical to the motor domains of different members of the kinesin gene family. Kinesins are molecular motor proteins that move along microtubules powered by ATP-hydrolysis. Conventional Kinesin consists of two Kinesin heavy chains (Khc) and two Kinesin light chains (Klc). Khc consists of a N-terminal motor domain, a central domain made up of heptad-repeats, and a C-terminal putative "cargo" domain thoughtto bind vesiclesto move them. The motor domain of Khc is sufficientto mediate ATP-dependent movement along microtubules in vitro.

FIG. 2(C) shows an alignment of the putative cos2 P-loop motif (N1) with those of representative members of the kinesin gene family, a consensus sequence for the family is shown at the bottom. Closed and shaded rectangles indicate identity and similarity, respectively. The four underlined residues are invariantwithin the kinesin gene family. The minus sign indicates an acidic residue and X the absence of a consensus residue. The percent identity between cos2 and the indicated kinesin family members is shown at the right.

Several motor domain motifs implicated in nucleotide (N)- or microtubule-binding are highly conserved within the kinesin family and are generally conserved in Cos2. For example, the nucleotide-binding motif 1 (N1 or P-loop) in Cos2 is 50% identical to the kinesin gene family consensus sequence. Four residues strictly conserved in the family are present in Cos2 but Cos2 residues R177 and Q179 are significantly different. The N2 motif, SSRSH, in Cos2 is replaced by SLPAH, while N3, DLAGS/TE, is conserved in Cos2. N4 is not present in Cos2. Although the residues required for microtubule-binding are not well defined, two motifs have been tentatively implicated: the strictly conserved DLL motif and the L12 motif. The L12 consensus sequence is φI/VPY/FRN/D (φ=hydrophobic residues), both the P and R residues are strictly conserved (Goldstein, 1993 Annu. Rev. Genet. 27, 319–51). In Cos2 the DLL motif is present while L12 is partially conserved, with the expected R being absent.

Cos2 expression priorto germ band extension. Polyclonal rat antisera were raised against N- and C-terminal portions of Cos2. Both antisera were affinity purified and used to probe blots of embryo protein extracts. Both antisera reveal a single band of 175 kD. Preimmune antisera do not detect any protein on these blots. Cos2 migrates much slower than its predicted size of 133 kD, perhaps due to post-translational modification. Both antisera also recognize endogenous and over-expressed Cos2 in the cytoplasm of Drosophila S2 cultured cells.

Both affinity purified antisera were used to assess the expression of Cos2 in early embryos and both give the same results. In syncytial stage embryos (stage 4), prior to cellularization, Cos2 is distributed uniformly within the cortical cytoplasm, at apical and basal focal planes. Anti-lamin antibody (green) outlines the nuclei. Cos2 is not detected within nuclei nor in association with microtubule spindles. In late syncytial blastoderm embryos just prior to cellularization Cos2 accumulates between, and apical to, nuclei. A lateral view shows Cos2 accumulation forming rays perpendicularto the surface of the embryo. Surface views along the apices of nuclei show Cos2 accumulation forming a honeycomb pattern. Cos2 is punctate rather than uniform within the honeycomb lattice.

Cos2 is associated with furrow canals throughout cellularization. Furrow canals (fc) are located at the leading edge of newly forming membrane between adjacent somatic nuclei. During cellularizationeach furrow canal moves toward the basal end of the nuclei where they broaden, forming expanded furrow canals (efc), and then fuse with one another in a process that will seal off the new cells from the embryo's interior. Cos2 is present at relatively high levels within each early furrow canal. At this time Cos2 is also distributed uniformly at lower levels throughout the cortical cytoplasm and along new membrane trailing each furrow canal. Cos2 is associated with expanded furrow canals prior to and after their fusion during late cellularization. In cellular blastoderm embryos and after the onset of gastrulation Cos2 is in the cytoplasm and at the periphery of all cells. Cos2 transcripts are uniformly distributed in the early embryo.

Cos2 levels are elevated in the anterior compartments of embryonic segments and imaginal discs. In contrast to the uniform distribution of cos2 mRNA in the germ band-extended embryo, Cos2 is present in a striped pattern. Faint stripes along the germ band are first observed in late stage 9 embryos and become prominent by stage 10. Each stripe is continuous along the dorsal-ventral axis in both the ectoderm and the underlying mesoderm. The stripes persist throughout stage 11 and decay during germ band retraction (stage 12). The stripes appear to form just anterior of parasegmental grooves in anterior compartment cells, but precise determination of boundaries is difficult due to weak signal.

The accumulation of Cos2 in imaginal discs is reminiscent of its expression in the germ band extended embryo. In situ hybridizations with single-stranded sense and antisense cos2 probes show that cos2 mRNA is uniform within wing discs. In contrast Cos2 levels are elevated in the anterior compartment. A ptc-lacZ enhancer trap stock (AT90), producing nuclear localized β-galactosidase (β-gal) in a ptc-specific pattern, was used to show that the position of the A/P border corresponds to the line of transition from high to low Cos2 levels.

The apparent elevation of Cos2 in the anterior could be due to higher protein levels, to differential fixation of Cos2, or to the accessibility of Cos2 to antibodies. We confirmed that the amount of protein is regulated by dissecting anterior and posterior portions of wing discs and measuring protein levels on blots. The amount of Cos2 (C2), Ci and Engrailed (E) protein was normalized to the amount of α-Tubulin (T) in the two fractions. Although Cos2 is present in the posteriordisc extract, it is less abundant than in the anterior disc extract in keeping with the histochemical staining result. The Cos2 detected in the posterior disc extract has a slower mobility than the anterior protein, suggesting it is a distinct post-translational form of Cos2. As expected, Ci and En were detected only in anterior and posterior disc extracts, respectively.

Cos2 and Ci associate with microtubules in embryo extracts. A hallmark of kinesins is the ability to bind taxol-stabilized microtubules. It was tested whether Cos2 from fly embryos also binds microtubules. Embryo extracts were supplemented with taxol and centrifuged to bring down microtubules and associated proteins. In the absence of taxol, Cos2, Kinesin heavy chain (Khc), and α-Tubulin are in the supernatant. In the presence of taxol, α-Tubulin is in the pellet, showing that microtubules have formed efficiently. While Cos2 pellets, Khc remains in the supernatant because kinesin does not bind microtubules in the presence of the ATP contributed by the embryo extract. In the presence of the non-hydrolyzableATP-analogue AMP-PNP, and apyrase which breaks down ATP, both Khc and Cos2 are in the microtubule pellet. Therefore, Cos2 binds microtubules in a taxol-dependent, ATP-insensitive manner, while Khc binds microtubules in a taxol-dependent,ATP-sensitive manner. A bacterially expressed Cos2-GST fusion protein, containing the putative motor domain, also binds to purified microtubules.

We also tested whether Ci associates with microtubules, since so much Ci is cytoplasmic. Ci associates with microtubules just as Cos2 does, in a taxol-dependent, ATP-insensitive manner. A slight amount of Ci sedimenting in the absence of taxol was not consistently observed.

The microtubule-association of Cos2 and Ci is stable in the presence of ATP. Microtubule pellets containing Cos2, Ci and Khc were washed and resuspended in the presence of taxol and 5 mM ATP and recentrifuged. Khc is partially extracted into the supernatant with just ATP, as expected. However, both Cos2 and Ci remain microtubule-associated in the presence of ATP. Cos2, Ci, and Khc are completely extracted from microtubules in the presence of 5 mM ATP and 0.5M KCl. Most microtubules dissolve in the high salt, but some remain intact. Shaggy/Zeste-white3(Sgg/Zw3) protein, a kinase not expected to bind microtubules, serves as a control. A slight amount of Sgg/Zw3 cosediments with microtubules.

Although a substantial fraction of the soluble Cos2 is microtubule-associated, some is not. Embryos stained with antibodies to α-Tubulin and Cos2 reveal an overlap between Cos2 and microtubules but not a strict colocalization. Presumably not all of the Cos2 is microtubule-associated in vivo, consistent with the in vitro microtubule-binding results.

Cos2 and Ci physically associate. The similar microtubule-association of Cos2 and Ci suggested the two proteins might be in a protein complex. It was tested whether Cos2 and Ci coelute from a gel filtration column. A S100 embryo extract was separated on a Sepharose 4B column and fractions were assayed for Cos2, Ci, and α-Tubulin by immunoblotting. The elution profiles for Cos2 and Ci are virtually identical. Their common peak fraction is approximately 500–600 kD. A homodimer of Cos2 is expected to elute with an approximate peak of 350 kD. α-Tubulin elutes with an apparent molecular weight of 110 kD, consistent with the expected size of α/β-Tubulin heterodimers. Because microtubules are efficiently depolymerized under the conditions used, the coelution of Cos2 and Ci is not dependent on microtubule-mediated crosslinking of the two proteins.

It was tested whether Cos2 and Ci are associated in a protein complex using immunoprecipitation. Anti-Cos2 and anti-Ci antibodies nearly completely precipitate Cos2 and Ci, respectively. A significant fraction of Ci is coprecipitated by anti-Cos2 antibodies and vice versa. Cos2 preimmune antisera alone do not precipitate Cos2 or Ci, nor do Protein G Sepharose beads alone.

cos2 somatic clones have increased cytoplasmic Ci staining and cause pattern duplications. The FLP recombinase-FRT technique was employed to generate homozygous clones of cos2 in wing discs and examine the location of Ci. Approximately 50% of flies genetically competent to form cos2 somatic clones display extra wing veins and/or dramatic mirror-image duplications characteristic of cos2 mutants. cos2 clones, marked by the loss of the Myc epitope carried on the other chromosome are frequently observed in both the A and P compartments of wing discs. Elevated cytoplasmic Ci staining is seen in cos2 clones in the A compartment. The level of Ci staining is independent of the clone's distance from the A/P border or size. Nuclear Ci is not evident in the clones. cos2 clones in the P compartment do not express ci.

Cos2 is a divergent member of the diverse kinesin gene family. The Cos2 sequence resembles kinesin, but Cos2 does not appear to belong to an existing kinesin subfamily and may have novel properties. Phylogenetic subfamilies have been established based on structural and functional similarities between motor domains. Some subfamilies are implicated in microtubule-based vesicle or organelle movement, while others participate in assembly or force generation for mitotic or meiotic microtubule spindles. The motor domain motifs implicated in nucleotide-binding in other kinesins are different in Cos2, so Cos2 may lack motor activity. Most kinesin motor proteins release microtubules when provided with ATP, an intrinsic property of the motor domain. In contrast, Cos2 remains attached to microtubules when exogenous ATP is provided. This suggests that unlike kinesin and many kinesin-related proteins, Cos2 may not regulate its binding to microtubules by ATP hydrolysis. The nucleotide-binding motifs of Cos2 may be unable to coordinate ATP.

The unconventional nature of Cos2 is also manifested in its localization in early embryos. Prior to somatic cell formation Cos2 accumulates in a honeycomb pattern at the cortex of the embryo. A similar lattice pattern is characteristic of actin and actin-associated proteins. Slightly later, during cellularization, Cos2 is associated with the actin-rich furrow canals, and the periphery of cells after cellularization. SMY1, a divergent kinesin-related protein, also localizes to actin-rich regions of the cell and has been implicated in two actin-based processes: polarized growth and secretion in yeast.

Cos2 levels are post-transcriptionally elevated in the anterior compartment. Because cos2 mRNA levels are uniform, the elevated level of Cos2 in the A cells must be due to differences between A and P cells in either the production or the stability of Cos2. The uniform level of Cos2 throughoutthe anterior compartment of imaginal discs is inconsistent with Hh signal regulating its accumulation. Hh regulates Ci post-transcriptionally in the anterior compartment, but the limited range of Hh results in a graded distribution of Ci across the anterior compartment quite unlike the Cos2 distribution. A uniform anterior- or posterior-specific activity could establish the high uniform level of Cos2 in the anterior compartment. One possibility is that the moderate level of Ci in all A cells is sufficient to stabilize Cos2 in a complex. In P cells Cos2 would turn over more rapidly because it is not protected by complex formation. Another possibility is that Ci heightens translation of cos2 mRNA, a possible role for the Ci zinc-finger protein in the cytoplasm. Alternativelya factor controlled by en could destroy Cos2 in P cells or stabilize it in A cells. cos2 is not required for patterning the posterior compartment, so the low level of Cos2 detected in the posterior disc extract may be non-functional.

Cos2 may directly inhibit Ci from activating Hh target genes. Previous genetic evidence indicates that cos2 functions in A cells to regulate Hh target gene expression. The findings described above are consistent with these genetic data. First, Cos2 accumulates to high levels in A cells. Second, Cos2 physically associates with Ci, which is expressed in A cells. Third, cos2 activity reduces Ci staining in A cells. cos2 somatic clones in the anterior compartment of wing discs express high levels of Ci and cause mirror-image duplications of the wing. These pattern duplications are predicted to result from Ci-mediated activation of dpp within cos2 clones. Cos2 and Ci may act in a large protein complex in the cytoplasm of A cells to mediate the regulation of Hh target genes.

The control of Hh target gene expression may depend on the level and/or post-translational form of Ci. When increased Ci is produced in wing discs far from the A/P border, beyond the influence of Hh, dpp and ptc transcription are activated in A cells. Because dpp and ptc are also activated in P cells, the Ci-mediated activation of these targets does not depend on an A compartment-specific factor. Ci may normally require a Hh-dependent modification to activate Hh targets, but elevated Ci seems sufficient to activate Hh targets. Along the A/P border Ci levels are post-transcriptionally elevated in response to Hh signalling. This elevated level of Ci is thought to allow it to enter the nucleus and directly activate Hh targets. Although nuclear Ci is hard to see, when the C-terminal portion of an epitope-tagged Ci is removed, leaving the zinc-fingers intact, Ci protein appears in the nucleus and the cytoplasm. Ci therefore appears competent to enter the nucleus but is normally restricted to the cytoplasm by the C-terminal tail. The absence of detectable Ci in the nucleus may be the result of inadequate Ci antibodies.

The protein complex we have identified could control the level of Ci and its subcellular distribution. The Cos2/Ci complex may control the level of Ci either by increasing Ci production or decreasing its degradation. The complex could protect Ci from proteases only when Hh signal is received, or the complex could associate with polysomes to facilitate translation of ci mRNA. Because a substantial fraction of Cos2 and Ci are associated, Cos2 may sequester Ci in the cytoplasm, possibly by tethering it to the cytoskeleton. Because Ci lacks an obvious nuclear localization signal its movement to the nucleus may be regulated by its ability to couple to a protein that carries it there. The transcription factor dCBP may serve this function. Cos2 may render Ci unavailable to such a protein except along the A/P border where Cos2 is inhibited. The absence of detectable nuclear Ci after eliminating cos2 function may result from redundancy in the retention of Ci in the cytoplasm and/or inadequate Ci antibodies.

The identification of the Cos2/Ci complex helps to fill in missing steps in Hh signaling by showing direct interactions among two of the five known signal transduction components and by providing a cytoskeletal link. The importance of the complex is further underscored by the presence of a third component, fused. The subcellular distribution of the complex may be important for controlling Hh targets and consequently cell differentiation.

In accordance with the subject invention, costal2 genes are provided, which can serve many purposes. The costal2 protein may be used in a screening for agonists and antagonists, and for assaying for the transcription of cos2 mRNA. The protein or fragments thereof may be used to produce antibodies specific for the protein or specific epitopes of the protein. In addition, the gene may be employed for investigating embryonic development, by screening fetal tissue, preparing transgenic animals to serve as models, and the like.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An isolated nucleic acid molecule other than a naturally occurring chromosome comprising a sequence encoding a Cos2 protein, wherein said Cos2 protein comprises the sequence set forth in SEQ ID NO:2.

2. An expression cassette comprising a transcriptional initiation region functional in an expression host, a nucleic acid having a sequence of the isolated nucleic acid according to claim 1 under the transcriptional regulation of said transcriptional initiation region, and a transcriptional termination region functional in said expression host.

3. A cell comprising an expression cassette according to claim 2 as part of an extrachromosomal element or integrated into the genome of a host cell as a result of introduction of said expression cassette into said host cell, and the cellular progeny of said host cell.

4. A method for producing cos2 protein, said method comprising:

growing a cell according to claim 3 whereby said cos2 protein is expressed; and isolating said cos2 protein free of other proteins.

5. A cell comprising a nucleic acid according to claim 1 as part of an extrachromosomal element or integrated into the genome of a host cell as a result of introduction of said expression cassette into said host cell, and the cellular progeny of said host cell.

6. An isolated nucleic acid comprising at least 50 contiguous nucleotides of the sequence of SEQ ID NO:1.

7. An isolated nucleic acid molecule other than a naturally occurring chromosome comprising a sequence encoding a Cos2 protein, wherein said Cos2 protein comprises the sequence set forth in SEQ ID NO:1.

* * * * *

SEQUENCE LISTING

<160> NUMBER OF SEQ ID NOS: 11

<210> SEQ ID NO 1
<211> LENGTH: 3605
<212> TYPE: DNA
<213> ORGANISM: D. Melanogaster

<400> SEQUENCE: 1

```
atggaaatac ccattcaggt agcggtgcgc atcttcccgc atagagagct caaggacttg      60
ttgaggagct tcggccccac agagcccaaa aaggatgcgc aggcggtgga tgagggggcg     120
gactccaagg actccgaggc tcaagttccg gcggctgaga aggacaatcc gtcaatttca     180
gagacggacc caaacgggaa tgctgagcag gacagtgcgg ccgattcgaa gacaattcca     240
gatgccaatg gcaacgacag tggtcagaag gattacccag actccgcata ttgcgttcag     300
gctattccca tcagcgcttc ggccctggga ttgcccagtg ccctgccagg cggagatccc     360
atggacagca ttgcagctgg actgatacaa gtcggtcccc acacggttcc ggtcacccac     420
gccctcccca gcagcagctc ccaggagcaa gtgtaccacc agacggtctt tccgctcatc     480
accctgttcc tggaaggttt cgacgcatct gtagtcacct atggcagag gggccagggc     540
aaaagctaca cactctacgg aaacgtccag gaccctactc tgacggattc caccgaagga     600
gtcgtccaac tttgtgtccg tgacattttc tcacacatat cgttgcaccc agaacgcacc     660
tatgccatca acgtgggatt cgtggaaatt tgcggaggtg atgtctgcga cttgttgggc     720
atgggaaaca tacactgcac caacgtagat gccgtcttcc actggttgca ggtgggtctg     780
tcggcccgcc aatcgttgcc ggcgcacacc ctgttcacgc ttaccctgga gcagcagtgg     840
gtgtccaagg aggggctgtt gcagcaccgc ttgtccacgg ccagtttctc ggatctctgc     900
ggcacagaga gatgtggcga ccagccaccg ggacgtcctc tcgatgctgg cctgtgtatg     960
ctggagcagg tgatcagtac tctcacagat ccaggcctca tgtacgggg taatggcaac    1020
attccgtacg gtcagaccac gctcaccact ctcctgaagg actcgttcgg cggacgggct    1080
cagacgctcg tgatcctgtg cgtgtcaccg ctggaagagc acttgcccga aactcttggc    1140
aacctgcagt tcgcctttaa ggtgcagtgc gtacgtaatt ttgtaattat gaacacctac    1200
tccgacgaca acacgatgat cgttcagccg gctgagcctg ttcccgaatc caattcctct    1260
gctggaccct tgtcgcaggc gggaccaggg gacaactttg gcctacaatt cgcagcgagc    1320
caatggtcca aactagttac caacgccgag gggctatttt ccaagctgat agactccaag    1380
ctaattactg aagtggagaa ggagcagatc gatgagtggc tcttcctcaa gcaggagtgc    1440
gaggagtgtc tcagctcaac agaggctatg cgtcagcaaa aacagttggt tcccattctg    1500
gaggccgagg agcccgagga cgtgaattct gaagcagcca attcggagtc gccaaactcc    1560
gacaacgaaa acgacacaga caatgagtcg catcggcccg atctggacga caagatagaa    1620
```

-continued

```
agtctaatgg aagagtttcg cgacaaaaca gacgctctta tacttgaaaa acacgctgaa    1680
tatctatcca agcatccgaa ggcggttatg caaagccaag accgcgagat tgaggcacag    1740
ccgccagaag aaaatggtga tgatcgaaaa gtcagcattg gcagtcgcag gagaagtgtt    1800
cagccaggtg ctagcttaag tactgctgag cttgccatgc ttaatcgggt agcttcccag    1860
cagccgcctc cgcccatcga tcctgagtcg gtcgtcgatc ctctgaaaag ttcttcgggc    1920
gaaggaatcc gtcaggcggc tctcgctgcc gccgccgcca ctgctcctat tgaacagctg    1980
cagaaaaaat tgcgcaaact ggtcgctgag atcgagggca acaacgaca gttacgggaa     2040 atcgaagaac aatccaggta aaacaaaata taatcgccga attggtcaag aacagcgata    2100
cacgcagcca tgcaaagcaa agatttcaca agaaacgtgc caaacttgag gccgagtgcg    2160
acaaggccaa gaagcagtta ggtaaggcgc tagttcaagg ccggggtcag tcggagattg    2220
agcgatggac cacgataatc ggacatctcg agcgtcgact agaagacctc agctcaatga    2280
agcatattgc gggtgagagc ggacagaagg tgaagaagct acagcaatcg gtgggcgagt    2340
cgcgaaaaca ggccgatgat ttacagaaaa agcttcgaaa ggagtgcaag ctgcgctgcc    2400
agatggaggc ggagctggtc aaactacgag aatccaggga gactggcaaa gagctagtga    2460
aggcgcaagg ttctcccgag caacaaggcc gccagttaaa ggcagtacag gctaggatta    2520
cgcaccttaa tcacatttta cgcgagaagt cggataacct ggagragcag ccgggaccag    2580
aacagcagga gaccttgcgt catgagatcc gcaacttgcg cggaactcgt gacttgttgt    2640
tgaaagaacg ctgtcatttg gaccgcaaac ttaagcggga caaggtgctg acgcaaaagg    2700
aggagcgcaa gctgctcgag tgcgatgagg ccatcgaggc catagatgcg gccatagaat    2760
tcaagaacga gatgatcacg ggccaccgct ccatcgacac gagcgaccga attcagcggg    2820 agaaggaga acagatgctg atggcacgcc taaatcgtct ctcaacggag gagatgcgaa     2880
cacttctgta caaatacttc acgaaggtta tcgatttgcg cgactcttca cgaaagctgg    2940
agctgcagct ggtgcagttg gagcgtgagc gggatgcctg ggagtggaag gagcgtgttc    3000
tgtccaatgc cgtgcgccag gctagactgg aaggcgaacg gaatgcggtg ctgctgcagc    3060
gccagcacga aatgaaactc actttgatgc tgcgtcacat ggcggaggaa acgtcggcca    3120
gttcggccag ctacggagaa cgagctttgg cccctgcctg tgtcgccccg ccggtgcagg    3180
ccagtagtga tttcgactac gatcatttct acaaaggtgg cggcaatcca agcaaggcac    3240
tgatcaaagc gccaaagccg atgcccaccg gctcggcgct agacaaatac aaggacaaag    3300
agcaacgcag cggacgcaac atctttgcca agttccatgt gctcaccaga tatgcgtcag    3360
ctgccgcagc cggttcctca gggtccacgg ccgaggaatc cacggccctg attgagtcaa    3420 ccaccacgggc cacggcaacc actacgtcga caaccaccac tggagccgta ggaaaagtga    3480
aggacaaggc cctggtcagc ttcaggccgg agcagctgaa gcgtctgatg ccagctccga    3540
cggccacgaa agtgacgcgt cagaagaaca agataattat ccaggacgca agtcgtcgaa    3600
actaa                                                               3605
```

<210> SEQ ID NO 2
<211> LENGTH: 1201
<212> TYPE: PRT
<213> ORGANISM: D. Melanogaster
<220> FEATURE:
<221> NAME/KEY: VARIANT
<222> LOCATION: (1)...(1201)
<223> OTHER INFORMATION: Xaa = Any Amino Acid -continued

```
<400> SEQUENCE: 2

Met Glu Ile Pro Ile Gln Val Ala Val Arg Ile Phe Pro His Arg Glu
 1               5                  10                  15

Leu Lys Asp Leu Leu Arg Ser Phe Gly Pro Thr Glu Pro Lys Lys Asp
             20                  25                  30

Ala Gln Ala Val Asp Glu Gly Ala Asp Ser Lys Asp Ser Glu Ala Gln
         35                  40                  45

Val Pro Ala Ala Glu Lys Asp Asn Pro Ser Ile Ser Glu Thr Asp Pro
 50                  55                  60

Asn Gly Asn Ala Glu Gln Asp Ser Ala Ala Asp Ser Lys Thr Ile Pro
 65                  70                  75                  80

Asp Ala Asn Gly Asn Asp Ser Gly Gln Lys Asp Tyr Pro Asp Ser Ala
                 85                  90                  95

Tyr Cys Val Gln Ala Ile Pro Ile Ser Ala Ser Ala Leu Gly Leu Pro
                100                 105                 110

Ser Ala Leu Pro Gly Gly Asp Pro Met Asp Ser Ile Ala Ala Gly Leu
            115                 120                 125

Ile Gln Val Gly Pro His Thr Val Pro Val Thr His Ala Leu Pro Ser
        130                 135                 140

Ser Ser Ser Gln Glu Gln Val Tyr His Gln Thr Val Phe Pro Leu Ile
145                 150                 155                 160

Thr Leu Phe Leu Glu Gly Phe Asp Ala Ser Val Val Thr Tyr Gly Gln
                165                 170                 175

Arg Gly Gln Gly Lys Ser Tyr Thr Leu Tyr Gly Asn Val Gln Asp Pro
            180                 185                 190

Thr Leu Thr Asp Ser Thr Glu Gly Val Val Gln Leu Cys Val Arg Asp
        195                 200                 205

Ile Phe Ser His Ile Ser Leu His Pro Glu Arg Thr Tyr Ala Ile Asn
    210                 215                 220

Val Gly Phe Val Glu Ile Cys Gly Gly Asp Val Cys Asp Leu Leu Gly
225                 230                 235                 240

Met Gly Asn Ile His Cys Thr Asn Val Asp Ala Val Phe His Trp Leu
                245                 250                 255

Gln Val Gly Leu Ser Ala Arg Gln Ser Leu Pro Ala His Thr Leu Phe
            260                 265                 270

Thr Leu Thr Leu Glu Gln Gln Trp Val Ser Lys Glu Gly Leu Leu Gln
        275                 280                 285

His Arg Leu Ser Thr Ala Ser Phe Ser Asp Leu Cys Gly Thr Glu Arg
    290                 295                 300

Cys Gly Asp Gln Pro Pro Gly Arg Pro Leu Asp Ala Gly Leu Cys Met
305                 310                 315                 320

Leu Glu Gln Val Ile Ser Thr Leu Thr Asp Pro Gly Leu Met Tyr Gly
                325                 330                 335

Val Asn Gly Asn Ile Pro Tyr Gly Gln Thr Leu Thr Thr Leu Leu
            340                 345                 350

Lys Asp Ser Phe Gly Gly Arg Ala Gln Thr Leu Val Ile Leu Cys Val
        355                 360                 365

Ser Pro Leu Glu Glu His Leu Pro Glu Thr Leu Gly Asn Leu Gln Phe
370                 375                 380

Ala Phe Lys Val Gln Cys Val Arg Asn Phe Val Ile Met Asn Thr Tyr
385                 390                 395                 400

Ser Asp Asp Asn Thr Met Ile Val Gln Pro Ala Glu Pro Val Pro Glu
                405                 410                 415
```

-continued

```
Ser Asn Ser Ser Ala Gly Pro Leu Ser Gln Ala Gly Pro Gly Asp Asn
            420                 425                 430

Phe Gly Leu Gln Phe Ala Ala Ser Gln Trp Ser Lys Leu Val Thr Asn
            435                 440                 445

Ala Glu Gly Leu Phe Ser Lys Leu Ile Asp Ser Lys Leu Ile Thr Glu
            450                 455                 460

Val Glu Lys Glu Gln Ile Asp Glu Trp Leu Phe Leu Lys Gln Glu Cys
465                 470                 475                 480

Glu Glu Cys Leu Ser Ser Thr Glu Ala Met Arg Gln Gln Lys Gln Leu
            485                 490                 495

Val Pro Ile Leu Glu Ala Glu Pro Glu Asp Val Asn Ser Glu Ala
            500                 505                 510

Ala Asn Ser Glu Ser Pro Asn Ser Asp Asn Glu Asn Asp Thr Asp Asn
            515                 520                 525

Glu Ser His Arg Pro Asp Leu Asp Asp Lys Ile Glu Ser Leu Met Glu
            530                 535                 540

Glu Phe Arg Asp Lys Thr Asp Ala Leu Ile Leu Glu Lys His Ala Glu
545                 550                 555                 560

Tyr Leu Ser Lys His Pro Lys Ala Val Met Gln Ser Gln Asp Arg Glu
            565                 570                 575

Ile Glu Ala Gln Pro Pro Glu Glu Asn Gly Asp Asp Arg Lys Val Ser
            580                 585                 590

Ile Gly Ser Arg Arg Arg Ser Val Gln Pro Gly Ala Ser Leu Ser Thr
            595                 600                 605

Ala Glu Leu Ala Met Leu Asn Arg Val Ala Ser Gln Gln Pro Pro Pro
            610                 615                 620

Pro Ile Asp Pro Glu Ser Val Val Asp Pro Leu Glu Ser Ser Ser Gly
625                 630                 635                 640

Glu Gly Ile Arg Gln Ala Ala Leu Ala Ala Ala Ala Thr Ala Pro
            645                 650                 655

Ile Glu Gln Leu Gln Lys Lys Leu Arg Lys Leu Val Ala Glu Ile Glu
            660                 665                 670

Gly Lys Gln Arg Gln Leu Arg Glu Ile Glu Glu Thr Ile Gln Val Lys
            675                 680                 685

Gln Asn Ile Ile Ala Glu Leu Val Lys Asn Ser Asp Thr Arg Ser His
            690                 695                 700

Ala Lys Gln Arg Phe His Lys Lys Arg Ala Lys Leu Glu Ala Glu Cys
705                 710                 715                 720

Asp Lys Ala Lys Lys Gln Leu Gly Lys Ala Leu Val Gln Gly Arg Gly
            725                 730                 735

Gln Ser Glu Ile Glu Arg Trp Thr Thr Ile Ile Gly His Leu Glu Arg
            740                 745                 750

Arg Leu Glu Asp Leu Ser Ser Met Lys His Ile Ala Gly Glu Ser Gly
            755                 760                 765

Gln Lys Val Lys Lys Leu Gln Gln Ser Val Gly Glu Ser Arg Lys Gln
            770                 775                 780

Ala Asp Asp Leu Gln Lys Lys Leu Arg Lys Glu Cys Lys Leu Arg Cys
785                 790                 795                 800

Gln Met Glu Ala Glu Leu Val Lys Leu Arg Glu Ser Arg Glu Thr Gly
            805                 810                 815

Lys Glu Leu Val Lys Ala Gln Gly Ser Pro Glu Gln Gln Gly Arg Gln
            820                 825                 830
```

-continued

Leu Lys Ala Val Gln Ala Arg Ile Thr His Leu Asn His Ile Leu Arg
        835                 840                 845

Glu Lys Ser Asp Asn Leu Glu Xaa Gln Pro Gly Pro Glu Gln Gln Glu
    850                 855                 860

Thr Leu Arg His Glu Ile Arg Asn Leu Arg Gly Thr Arg Asp Leu Leu
865                 870                 875                 880

Leu Lys Glu Arg Cys His Leu Asp Arg Lys Leu Lys Arg Asp Lys Val
                885                 890                 895

Leu Thr Gln Lys Glu Glu Arg Lys Leu Leu Glu Cys Asp Glu Ala Ile
            900                 905                 910

Glu Ala Ile Asp Ala Ala Ile Glu Phe Lys Asn Glu Met Ile Thr Gly
        915                 920                 925

His Arg Ser Ile Asp Thr Ser Asp Arg Ile Gln Arg Glu Lys Gly Glu
    930                 935                 940

Gln Met Leu Met Ala Arg Leu Asn Arg Leu Ser Thr Glu Glu Met Arg
945                 950                 955                 960

Thr Leu Leu Tyr Lys Tyr Phe Thr Lys Val Ile Asp Leu Arg Asp Ser
                965                 970                 975

Ser Arg Lys Leu Glu Leu Gln Leu Val Gln Leu Glu Arg Glu Arg Asp
            980                 985                 990

Ala Trp Glu Trp Lys Glu Arg Val Leu Ser Asn Ala Val Arg Gln Ala
        995                 1000                1005

Arg Leu Glu Gly Glu Arg Asn Ala Val Leu Leu Gln Arg Gln His Glu
    1010                1015                1020

Met Lys Leu Thr Leu Met Leu Arg His Met Ala Glu Glu Thr Ser Ala
1025                1030                1035                1040

Ser Ser Ala Ser Tyr Gly Glu Arg Ala Leu Ala Pro Ala Cys Val Ala
                1045                1050                1055

Pro Pro Val Gln Ala Ser Ser Asp Phe Asp Tyr Asp His Phe Tyr Lys
            1060                1065                1070

Gly Gly Gly Asn Pro Ser Lys Ala Leu Ile Lys Ala Pro Lys Pro Met
        1075                1080                1085

Pro Thr Gly Ser Ala Leu Asp Lys Tyr Lys Asp Lys Glu Gln Arg Ser
    1090                1095                1100

Gly Arg Asn Ile Phe Ala Lys Phe His Val Leu Thr Arg Tyr Ala Ser
1105                1110                1115                1120

Ala Ala Ala Ala Gly Ser Ser Gly Ser Thr Ala Glu Glu Ser Thr Ala
                1125                1130                1135

Leu Ile Glu Ser Thr Thr Thr Ala Thr Ala Thr Thr Ser Thr Thr
            1140                1145                1150

Thr Thr Gly Ala Val Gly Lys Val Lys Asp Lys Ala Leu Val Ser Phe
        1155                1160                1165

Arg Pro Glu Gln Leu Lys Arg Leu Met Pro Ala Pro Thr Ala Thr Lys
    1170                1175                1180

Val Thr Arg Gln Lys Asn Lys Ile Ile Ile Gln Asp Ala Ser Arg Arg
1185                1190                1195                1200

Asn

<210> SEQ ID NO 3
<211> LENGTH: 24
<212> TYPE: PRT
<213> ORGANISM: D. Melanogaster

<400> SEQUENCE: 3

-continued

```
Leu Arg Gly Phe Asp Ala Ser Val Val Thr Tyr Gly Gln Arg Gly Gln
 1               5                  10                  15

Gly Lys Ser Tyr Thr Leu Tyr Gly
            20

<210> SEQ ID NO 4
<211> LENGTH: 24
<212> TYPE: PRT
<213> ORGANISM: UNKNOWN

<400> SEQUENCE: 4

Leu Ala Gly Tyr Asn Gly Thr Thr Phe Ala Tyr Gly Gln Thr Gln Thr
 1               5                  10                  15

Gly Lys Thr Tyr Thr His Ser Gly
            20

<210> SEQ ID NO 5
<211> LENGTH: 24
<212> TYPE: PRT
<213> ORGANISM: UNKNOWN

<400> SEQUENCE: 5

Leu Glu Gly Tyr Asn Gly Thr Ile Phe Ala Tyr Gly Gln Thr Ser Ser
 1               5                  10                  15

Gly Lys Thr His Thr Met Glu Gly
            20

<210> SEQ ID NO 6
<211> LENGTH: 24
<212> TYPE: PRT
<213> ORGANISM: UNKNOWN

<400> SEQUENCE: 6

Leu Glu Gly Tyr Asn Gly Thr Ile Phe Ala Tyr Gly Gln Thr Gly Thr
 1               5                  10                  15

Gly Lys Thr Phe Thr Met Glu Gly
            20

<210> SEQ ID NO 7
<211> LENGTH: 23
<212> TYPE: PRT
<213> ORGANISM: UNKNOWN

<400> SEQUENCE: 7

Leu Asp Gly Tyr Asn Val Cys Ile Phe Cys Tyr Gly Gln Thr Gly Ser
 1               5                  10                  15

Gly Lys Thr His Thr Met Ser
            20

<210> SEQ ID NO 8
<211> LENGTH: 23
<212> TYPE: PRT
<213> ORGANISM: UNKNOWN

<400> SEQUENCE: 8

Leu Asn Gly Tyr Asn Gly Thr Val Ile Thr Tyr Pro Ser Phe Ser Gly
 1               5                  10                  15

Lys Ser Tyr Ser Leu Ile Gly
            20

<210> SEQ ID NO 9
<211> LENGTH: 24
```

```
<212> TYPE: PRT
<213> ORGANISM: UNKNOWN

<400> SEQUENCE: 9

Phe Glu Gly Tyr Asn Val Cys Ile Phe Ala Tyr Gly Gln Thr Gly Ser
 1               5                  10                  15

Gly Lys Ser Tyr Thr Met Met Gly
            20

<210> SEQ ID NO 10
<211> LENGTH: 23
<212> TYPE: PRT
<213> ORGANISM: UNKNOWN

<400> SEQUENCE: 10

Leu Ala Gly Tyr Asn Gly Thr Ile Phe Ala Tyr Gln Thr Ser Ser Gly
 1               5                  10                  15

Lys Thr His Thr Met Glu Gly
            20

<210> SEQ ID NO 11
<211> LENGTH: 23
<212> TYPE: PRT
<213> ORGANISM: CONSENSUS
<220> FEATURE:
<221> NAME/KEY: VARIANT
<222> LOCATION: (1)...(23)
<223> OTHER INFORMATION: Xaa = Any Amino Acid

<400> SEQUENCE: 11

Leu Gly Tyr Asn Xaa Thr Ile Phe Ala Tyr Gly Gln Thr Gly Ser Gly
 1               5                  10                  15

Lys Thr Tyr Thr Met Xaa Gly
            20
```